Oct. 14, 1958 F. MEILLAND Plant Pat. 1,759
ROSE PLANT
Filed Feb. 26, 1958
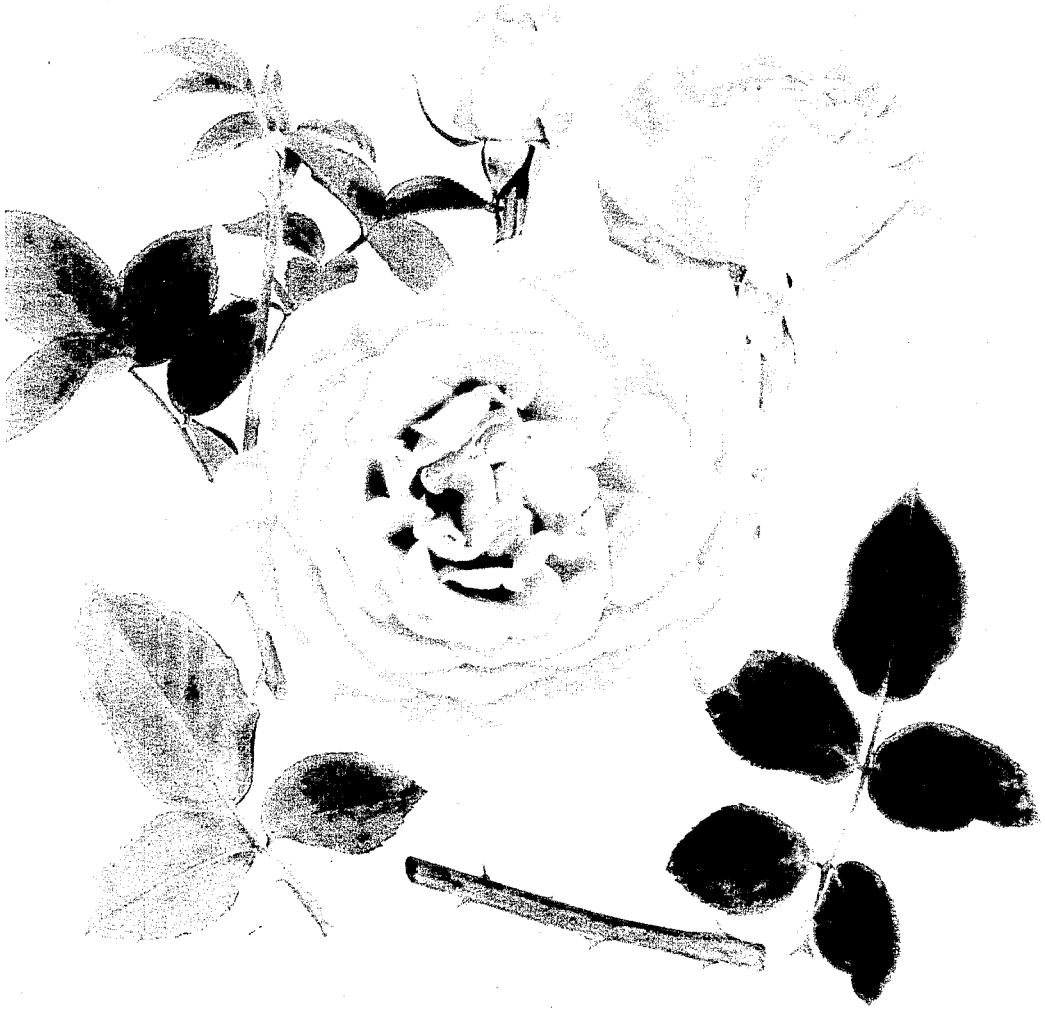
Inventor.
Francis Meilland
By: Robert Cobb
Attorneys.

United States Patent Office

Plant Pat. 1,759
Patented Oct. 14, 1958

1,759

ROSE PLANT

Francis Meilland, Cap d'Antibes, Alpes Maritimes, France, assignor to The Conard-Pyle Company, West Grove, Pa., a corporation of Pennsylvania Application February 26, 1958, Serial No. 717,797

1 Claim. (Cl. 47—61)

The present invention relates to a new and distinct variety of rose plant of the hybrid tea class, which was originated by me by crossing an unnamed and unpatented seedling derived from a cross of the variety "Peace" (U. S. Plant Patent No. 591) × the variety "Monique" (unpatented), with an unnamed and unpatented seedling derived from a cross of the variety "Peace" × the variety "Mrs. John Laing" (unpatented).

The primary objective of this breeding was to produce a new rose variety which combines the most desirable characteristics of its grandparents. This objective was fully achieved, along with other improvements, as evidenced by the following unique combination of outstanding features which differentiate the new variety from its ancestors, as well as from all other varieties of which I am aware:

(1) Exceptional vigor, accompanied by a good habit;

(2) Excellent foliage, which has better than average resistance to the common rose fungus diseases;

(3) Unusual floriferousness and continuity of bloom, which is exceptional for a variety which bears blooms of such large size;

(4) Outstanding size of the mature blooms, accompanied by the excellent form and good fragrance; and (5) A general flower color tonality of Rose Bengal, which remains relatively constant throughout the life of the blooms.

The foregoing features represent a substantial improvement over all other existing pink hybrid tea roses presently available in commerce, and asexual reproduction of the new variety by budding, as performed in France and at West Grove, Pennsylvania, U. S. A., shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—An unnamed seedling of "Peace" × "Monique."

*Pollen parent.*—An unnamed seedling of "Peace" × "Mrs. John Laing."

Propagation: Holds its distinguishing characteristics through succeeding propagations by budding.

*Flower*

Locality where grown and observed: West Grove, Pennsylvania, U. S. A.

Flowers borne: Singly to stem; on strong, long stems.

Quantity of bloom: Free, outdoors.

Continuity: Continuous.

Fragrance: Strong. Nature—tea.

Bud:

*Peduncle.*—Medium length; heavy; erect; rough; with medium number of red hairs. Color—green.

*Before calyx breaks.*—Size—medium. Form—medium long; ovoid; with a conspicuous neck; without foliaceous appendages on the surface of the bud; with slender, medium-cut foliaceous parts extending beyond the tip of the bud equal to ¼ or more of its length.

*As calyx breaks.*—Color—Spinel Red, Plate 0023, occasionally streaked with Maroon, Plate 1030.

*As first petal opens.*—Size—large. Form—medium long; pointed-ovoid. Color: outside—Spinel Red, Plate 0023, shading to small area of Yellow Ochre, Plate 07/3 at base of petal, with point of attachment Sulphur Yellow, Plate 1/1; inside—Rose Bengal, Plate 25, shading to Aureolin, Plate 3 at base.

*Opening.*—Opens up well.

Bloom:

*Size (when fully open).*—From 5 inches to 5½ inches.

*Petalage.*—Very double; from 60 to 65 petals; arranged regularly.

*Form.*—Very full at first, but becoming cupped; petals at first being rolled outward, and remaining rolled outward at maturity.

Petals: Medium thick; with inside satiny and outside shiny.

*Shape.*—Outer—round-ovate, with one or two notches. Intermediate—ovate, with one or two notches. Inner—ovate, and sometimes with one notch, but sometimes with no notches.

This description of a newly opened flower was made from a rose grown outdoors in the month of August, at West Grove, Pennsylvania, U. S. A.:

*Color.*—Outer petal: outside surface—between Solferino Purple, Plate 26/1 and Solferino Purple, Plate 26/2, shading to Spinel Pink, Plate 0625/1, with point of attachment Sulphur Yellow, Plate 1/2; inside surface—Rose Bengal, Plate 25/1, with margin Solferino Purple, Plate 26/1, and with point of attachment Sulphur Yellow, Plate 1/2. Intermediate petal: outside surface—Spirea Red, Plate 025/2, with point of attachment Sulphur Yellow, Plate 1/2; inside surface—Solferino Purple, Plate 26/1, shading to Rose Bengal, Plate 25/1, with point of attachment Sulphur Yellow, Plate 1/2. Inner petal: outside surface—Spinel Red, Plate 0023/1, with point of attachment Sulphur Yellow, Plate 1/2, sometimes bisected by a greenish vein; inside surface—Spirea Red, Plate 025, with point of attachment Dresden Yellow, Plate 64.

This description was made from a rose that was open for 3 days outdoors in the month of August, at West Grove, Pennsylvania, U. S. A.:

*Color.*—Outer petal: outside surface—Solferino Purple, Plate 26/2, shading to Spinel Pink; Plate 0625/1, and veined over lower quarter with Spinel Pink, Plate 0625, with point of attachment Sulphur Yellow, Plate 1/2; inside surface—Solferino Purple, Plate 26, with point of attachment Sulphur Yellow, Plate 1/2, and edge of petal showing a very narrow margin of white. Inner petal: outside surface—Spinel Pink, Plate 0625/1, with point of attachment Sulphur Yellow, Plate 1/2, and with most petals showing a narrow band of Naples Yellow, Plate 403 bisecting the petal from base to apex; inside surface—Spirea Red, Plate 025, with edge of petal showing a very narrow margin of white and with point of attachment Sulphur Yellow, Plate 1/2.

*General color effect.*—Newly opened flower—Rose Bengal, Plate 25/1, with edges of outer petals showing Solferino Purple, Plate 26/1. 3-days open—Solferino Purple, Plate 26, with edges of petals showing a very narrow margin of white.

*Behavior.*—Drop off cleanly.

*Flower longevity.*—On bush in garden—4 days in August. Cut roses grown outdoors and kept at living-room temperature—3 or 4 days in August.

*Reproductive Organs.*

Stamens: Many; arranged regularly about pistils.

Filaments: Many; most with anthers; medium length. Color—Carmine Rose, Plate 621, shading to Indian Yellow, Plate 6/1, at base.

Anthers: All open at once; medium size; seldom an anther fused with a petaloid. Color—Mimosa Yellow, Plate 602/1 before opening.

Pollen: Sparse. Color—gold.

Pistils: Medium number.

Styles: Uneven; medium length; medium caliper; bunched.

Stigma: Color—white yellow.

Ovaries: All enclosed in receptacle.

Hips: Medium length; globular; with inconspicuous neck; moderately rough; walls thick and fleshy. Color—green.

Sepals: Permanent; long; spear-shaped.

Seeds: Medium number; large.

*Plant*

Foliage:

*Leaves.*—Normal abundance; medium large; leathery.

*Leaflets.*—Shape—oval, with apex acute or acuminate. Base—obtuse. Margin—Simply serrate.

*Color.*—Mature: upper surface—Parsley Green, Plate 00962; under surface—Willow Green, Plate 000862/1. Young: upper surface—Lettuce Green, Plate 861/3, with adjoining midrib lightly overlaid with Oxblood Red, Plate 00823/3; under surface—Slightly lighter than Oxblood Red, Plate 00823/3, with veins showing Pod Green, Plate 061.

*Rachis (the supporting stem of the compound leaf).*—Medium caliper. Upper side—hairy. Under side—sparsely thorny.

*Stipules.*—Moderately long; medium width; with short points turning out at an angle of more than 45°.

*Disease resistance.*—Better than average resistance to mildew and blackspot, as compared with other varieties grown under the same cultural conditions at West Grove, Pennsylvania, U. S. A.

Growth:

*Habit.*—Bushy; upright; branched.

*Growth.*—Vigorous.

*Canes.*—Medium caliper.

*Main stems.*—Bright. Color—Fern Green, Plate 0862. Prickles—few; color—Fern Green, Plate 0862, lightly overlaid with a variable reddish brown color. Hairs—none.

*Branches.*—Bright. Color—Fern Green, Plate 0862. Prickles—several; color—Fern Green, Plate 0862, lightly overlaid with a reddish brown color. Hairs—none.

*New shoots.*—Dull. Color—Pod Green, Plate 061, lightly overlaid with Oxblood Red, Plate 00823/3. Prickles—several; color—Oxblood Red, Plate 00823/3. Hairs—none.

I claim:

A new and distinct variety of rose plant of the hybrid tea class, substantially as herein shown and described, characterized particularly as to novelty by its unique combination of exceptional vigor and good habit, excellent foliage having better than average resistance to mildew and blackspot, unusual floriferousness and continuity of bloom, outstanding size of the mature blooms accompanied by excellent form and good fragrance, and a distinctive Rose Bengal general color tonality of the blooms which remains relatively constant throughout the life of the blooms.

No references cited.